US009060708B2

(12) United States Patent
Robertson et al.

(10) Patent No.: US 9,060,708 B2
(45) Date of Patent: Jun. 23, 2015

(54) MULTI-MODE COMMUNICATION INGESTIBLE EVENT MARKERS AND SYSTEMS, AND METHODS OF USING THE SAME

(71) Applicant: Proteus Digital Health, Inc., Redwood City, CA (US)

(72) Inventors: Timothy Robertson, Belmont, CA (US); Mark Zdeblick, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 14/341,621

(22) Filed: Jul. 25, 2014

(65) Prior Publication Data
US 2015/0048929 A1    Feb. 19, 2015

Related U.S. Application Data

(63) Continuation of application No. 13/888,190, filed on May 6, 2013, now Pat. No. 8,810,409, which is a continuation of application No. 13/564,479, filed on Aug. 1, 2012, now Pat. No. 8,542,123, which is a (Continued)

(51) Int. Cl.
*H04Q 5/22* (2006.01)
*A61B 5/07* (2006.01)

(Continued)

(52) U.S. Cl.
CPC ............... *A61B 5/073* (2013.01); *A61B 5/0031* (2013.01); *A61B 5/4839* (2013.01); *A61B 2562/08* (2013.01); *A61B 2562/162* (2013.01); *H04B 5/0062* (2013.01); *A61B 5/4848* (2013.01); *G06K 7/10297* (2013.01)

(58) Field of Classification Search
None
See application file for complete search history.

(56) References Cited

U.S. PATENT DOCUMENTS 3,589,943 A   6/1971   Grubb et al.
3,607,788 A   9/1971   Adolph (Continued)

FOREIGN PATENT DOCUMENTS

CN    1991868      7/2007
CN    101005470    7/2007

(Continued)

OTHER PUBLICATIONS

Aade, "Aade 37th Annual Meeting San Antonio Aug. 4-7, 2010" American Association of Diabetes Educators Aug. (2010); http://www.diabeteseducator.org/annualmeeting/2010/index.html; 2 pp.

(Continued)

*Primary Examiner* — Travis Hunnings
(74) *Attorney, Agent, or Firm* — K&L Gates LLP

(57) ABSTRACT

Aspects of the invention include multi-mode communication ingestible event marker devices. Ingestible event marker devices of the invention include an ingestible component comprising a conductive communication module and at least one additional non-conductive communication module. The non-conductive communication module may be integrated with the ingestible component or at least a portion or all of the non-conductive communication module may be associated with a packaging component of the ingestible event marker device. Additional aspects of the invention include systems that include the devices and one or more receivers, as well as methods of using the same.

30 Claims, 13 Drawing Sheets

Related U.S. Application Data continuation of application No. 12/398,941, filed on Mar. 5, 2009, now Pat. No. 8,258,962.

(60) Provisional application No. 61/034,085, filed on Mar. 5, 2008.

(51) Int. Cl.
   *H04B 5/00* (2006.01)
   *G06K 7/10* (2006.01)
   *A61B 5/00* (2006.01)

(56) References Cited

U.S. PATENT DOCUMENTS

| | | |
|---|---|---|
| 3,628,669 A | 12/1971 | McKinnis et al. |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,564,363 A | 1/1986 | Bagnall et al. |
| 4,578,061 A | 3/1986 | Lemelson |
| 4,635,641 A | 1/1987 | Hoffman |
| 4,654,165 A | 3/1987 | Eisenberg |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,809,705 A | 3/1989 | Ascher |
| 4,844,076 A | 7/1989 | Lesho |
| 4,871,974 A | 10/1989 | Davis et al. |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,179,578 A | 1/1993 | Ishizu |
| 5,245,332 A | 9/1993 | Katzenstein et al. |
| 5,261,402 A | 11/1993 | DiSabito |
| 5,263,481 A | 11/1993 | Axelgaard et al. |
| 5,279,607 A | 1/1994 | Schentag et al. |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,485,841 A | 1/1996 | Watkin et al. |
| 5,511,548 A | 4/1996 | Riazzi et al. |
| 5,567,210 A | 10/1996 | Bates et al. |
| 5,596,302 A | 1/1997 | Mastrocola et al. |
| D377,983 S | 2/1997 | Sabri et al. |
| 5,600,548 A | 2/1997 | Nguyen et al. |
| 5,634,466 A | 6/1997 | Gruner |
| 5,634,468 A | 6/1997 | Platt |
| 5,645,063 A | 7/1997 | Straka et al. |
| 5,705,189 A | 1/1998 | Lehmann et al. |
| 5,720,771 A | 2/1998 | Snell |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,921,925 A | 7/1999 | Cartmell et al. |
| 5,925,030 A | 7/1999 | Gross et al. |
| 5,925,066 A | 7/1999 | Kroll et al. |
| 5,957,854 A | 9/1999 | Besson et al. |
| 5,963,132 A | 10/1999 | Yoakum et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |
| 6,090,489 A | 7/2000 | Hayakawa et al. |
| 6,091,975 A | 7/2000 | Daddona et al. |
| 6,095,985 A | 8/2000 | Raymond et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,953 B1 | 5/2002 | Devlin et al. |

(56) References Cited

U.S. PATENT DOCUMENTS

| | | |
|---|---|---|
| 6,394,997 B1 | 5/2002 | Lemelson |
| 6,409,674 B1 | 6/2002 | Brockway et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,505,077 B1 | 1/2003 | Kast et al. |
| 6,526,315 B1 | 2/2003 | Inagawa |
| 6,531,026 B1 | 3/2003 | Takeichi et al. |
| 6,540,699 B1 | 4/2003 | Smith |
| 6,544,174 B2 | 4/2003 | West |
| 6,564,079 B1 | 5/2003 | Cory |
| 6,572,636 B1 | 6/2003 | Hagen et al. |
| 6,574,425 B1 | 6/2003 | Weiss et al. |
| 6,577,893 B1 | 6/2003 | Besson el al. |
| 6,579,231 B1 | 6/2003 | Phipps |
| 6,595,929 B2 | 7/2003 | Stivoric |
| 6,599,284 B2 | 7/2003 | Faour et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,650,718 B1 | 11/2003 | Fujimura et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,683,493 B1 | 1/2004 | Fujimora et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,773,429 B2 | 8/2004 | Sheppard et al. |
| 6,800,060 B2 | 10/2004 | Marshall |
| 6,801,137 B2 | 10/2004 | Eggers et al. |
| 6,804,558 B2 | 10/2004 | Haller et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | von Alten |
| 6,937,150 B2 | 8/2005 | Medema |
| 6,939,292 B2 | 9/2005 | Mizuno |
| 6,942,616 B2 | 9/2005 | Kerr, II |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,023,940 B2 | 4/2006 | Nakamura et al. |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,050,419 B2 | 5/2006 | Azenkot et al. |
| 7,076,437 B1 | 7/2006 | Levy |
| 7,081,693 B2 | 7/2006 | Hamel et al. |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi |
| 7,261,690 B2 | 8/2007 | Teller. |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,295,877 B2 | 11/2007 | Govari |
| 7,313,163 B2 | 12/2007 | Liu et al. |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,366,675 B1 | 4/2008 | Walker et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |

(56) References Cited

U.S. PATENT DOCUMENTS

| | | |
|---|---|---|
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,502,643 B2 | 3/2009 | Farringdon et al. |
| 7,505,795 B1 | 3/2009 | Lim et al. |
| 7,508,248 B2 | 3/2009 | Yoshida |
| 7,510,121 B2 | 3/2009 | Koenck |
| 7,512,448 B2 | 3/2009 | Malick |
| 7,512,860 B2 | 3/2009 | Miyazaki et al. |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,616,710 B2 | 11/2009 | Kim |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,689,437 B1 | 3/2010 | Teller et al. |
| 7,697,994 B2 | 4/2010 | VanDanacker et al. |
| 7,712,288 B2 | 5/2010 | Ramasubramanian et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,779,614 B1 | 8/2010 | McGonagle et al. |
| 7,796,043 B2 | 9/2010 | Euliano et al. |
| 7,797,033 B2 | 9/2010 | D'Andrea et al. |
| 7,806,852 B1 | 10/2010 | Jurson |
| 7,809,399 B2 | 10/2010 | Lu |
| 7,844,341 B2 | 11/2010 | Von Arx et al. |
| 7,857,766 B2 | 12/2010 | Lasater et al. |
| 7,899,526 B2 | 3/2011 | Benditt et al. |
| 7,904,133 B2 | 3/2011 | Gehman et al. |
| D639,437 S | 6/2011 | Bishay et al. |
| 7,978,064 B2 | 7/2011 | Zdeblick et al. |
| 8,025,149 B2 | 9/2011 | Sterry et al. |
| 8,036,731 B2 | 10/2011 | Kimchy et al. |
| 8,036,748 B2 | 10/2011 | Zdeblick et al. |
| 8,073,707 B2 | 12/2011 | Teller et al. |
| 8,083,128 B2 | 12/2011 | Dembo et al. |
| 8,123,576 B2 | 2/2012 | Kim |
| 8,180,425 B2 | 5/2012 | Selvitelli et al. |
| 8,200,320 B2 | 6/2012 | Kovacs |
| 8,214,007 B2 | 7/2012 | Baker et al. |
| 8,224,667 B1 | 7/2012 | Miller et al. |
| 8,238,998 B2 | 8/2012 | Park |
| 8,249,686 B2 | 8/2012 | Libbus et al. |
| 8,258,962 B2* | 9/2012 | Robertson et al. ......... 340/573.1 |
| 8,285,356 B2 | 10/2012 | Bly et al. |
| 8,290,574 B2 | 10/2012 | Feild et al. |
| 8,301,232 B2 | 10/2012 | Albert et al. |
| 8,308,640 B2 | 11/2012 | Baldus et al. |
| 8,315,687 B2 | 11/2012 | Cross et al. |
| 8,369,936 B2 | 2/2013 | Farringdon et al. |
| 8,386,009 B2 | 2/2013 | Lindberg et al. |
| 8,389,003 B2 | 3/2013 | Mintchev et al. |
| 8,404,275 B2 | 3/2013 | Habboushe |
| 8,440,274 B2 | 5/2013 | Wang |
| 8,514,086 B2 | 8/2013 | Harper et al. |
| 8,542,123 B2* | 9/2013 | Robertson et al. ......... 340/573.1 |
| 8,564,432 B2 | 10/2013 | Covannon et al. |
| 8,597,186 B2 | 12/2013 | Hafezi et al. |
| 8,668,645 B2 | 3/2014 | Drucker et al. |
| 8,771,183 B2 | 7/2014 | Sloan |
| 8,810,409 B2* | 8/2014 | Robertson et al. ......... 340/573.1 |
| 8,932,221 B2 | 1/2015 | Colliou et al. |
| 2001/0027331 A1 | 10/2001 | Thompson |
| 2001/0031071 A1 | 10/2001 | Nichols et al. |
| 2001/0044588 A1 | 11/2001 | Mault |
| 2001/0051766 A1 | 12/2001 | Gazdzinski |
| 2001/0056262 A1 | 12/2001 | Cabiri et al. |
| 2002/0002326 A1 | 1/2002 | Causey et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0138009 A1 | 9/2002 | Brockway et al. |
| 2002/0192159 A1 | 12/2002 | Reitberg |
| 2002/0193669 A1 | 12/2002 | Glukhovsky |
| 2002/0193846 A1 | 12/2002 | Pool et al. |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0229382 A1 | 12/2003 | Sun et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0111011 A1 | 6/2004 | Uchiyama et al. |
| 2004/0115507 A1 | 6/2004 | Potter et al. |
| 2004/0115517 A1 | 6/2004 | Fukuda et al. |

(56) References Cited

U.S. PATENT DOCUMENTS

| | | |
|---|---|---|
| 2004/0121015 A1 | 6/2004 | Chidlaw et al. |
| 2004/0122297 A1 | 6/2004 | Stahmann et al. |
| 2004/0138558 A1 | 7/2004 | Dunki-Jacobs et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0171914 A1 | 9/2004 | Avni |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2004/0267240 A1 | 12/2004 | Gross et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0151625 A1 | 7/2005 | Lai |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0285607 A1 | 12/2006 | Strodtbeck et al. |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |

(56) References Cited

U.S. PATENT DOCUMENTS

| | | |
|---|---|---|
| 2007/0179371 A1 | 8/2007 | Peyser et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1* | 10/2007 | Jones et al. .............. 424/9.2 |
| 2007/0244370 A1 | 10/2007 | Kuo et al. |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0004503 A1 | 1/2008 | Nisani et al. |
| 2008/0014866 A1 | 1/2008 | Lipowski |
| 2008/0015421 A1 | 1/2008 | Penner |
| 2008/0015494 A1 | 1/2008 | Santini et al. |
| 2008/0015893 A1 | 1/2008 | Miller et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | DellaVecchia et al. |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemiec et al. |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1* | 5/2008 | Trovato .............. 250/506.1 |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1* | 7/2008 | Jones et al. .............. 424/452 |
| 2008/0183245 A1 | 7/2008 | Van Oort |
| 2008/0188837 A1 | 8/2008 | Belsky et al. |
| 2008/0194912 A1* | 8/2008 | Trovato et al. .............. 600/118 |
| 2008/0208009 A1 | 8/2008 | Shklarski |
| 2008/0214901 A1 | 9/2008 | Gehman |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1* | 10/2008 | Trovato et al. .............. 604/20 |
| 2008/0275312 A1 | 11/2008 | Mosesov |
| 2008/0281636 A1 | 11/2008 | Jung et al. |
| 2008/0284599 A1* | 11/2008 | Zdeblick et al. .............. 340/572.1 |
| 2008/0288026 A1 | 11/2008 | Cross et al. |
| 2008/0288027 A1* | 11/2008 | Kroll et al. .............. 607/60 |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling et al. |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boyden et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0134181 A1 | 5/2009 | Wachman et al. |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |

(56) References Cited

U.S. PATENT DOCUMENTS

| | | | |
|---|---|---|---|
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1* | 9/2009 | Robertson et al. ............... 455/39 |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1* | 12/2009 | Trovato et al. ............... 604/891.1 |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0033324 A1 | 2/2010 | Shimizu et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1* | 4/2010 | Zdeblick et al. ............... 600/302 |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0185055 A1 | 7/2010 | Robertson et al. |
| 2010/0191073 A1 | 7/2010 | Tarassenko et al. |
| 2010/0203394 A1 | 8/2010 | Bae et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1 | 10/2010 | Hunter et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1* | 11/2010 | Hafezi et al. ............... 600/302 |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312577 A1 | 12/2010 | Goodnow et al. |
| 2010/0312580 A1 | 12/2010 | Tarassenko et al. |
| 2010/0332443 A1 | 12/2010 | Gartenberg |
| 2011/0004079 A1 | 1/2011 | Al-Ali et al. |
| 2011/0009715 A1 | 1/2011 | O'Reilly et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0065983 A1* | 3/2011 | Hafezi et al. ............... 600/101 |
| 2011/0077660 A1 | 3/2011 | Janik et al. |
| 2011/0081860 A1 | 4/2011 | Brown et al. |
| 2011/0105864 A1* | 5/2011 | Robertson et al. ............... 600/302 |
| 2011/0124983 A1 | 5/2011 | Kroll et al. |
| 2011/0144470 A1 | 6/2011 | Mazar et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0279963 A1 | 11/2011 | Kumar et al. |
| 2012/0024889 A1 | 2/2012 | Robertson et al. |
| 2012/0029309 A1 | 2/2012 | Paquet et al. |
| 2012/0062371 A1 | 3/2012 | Radivojevic et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0197144 A1 | 8/2012 | Christ et al. |
| 2012/0214140 A1 | 8/2012 | Brynelsen et al. |
| 2012/0265544 A1 | 10/2012 | Hwang et al. |
| 2012/0299723 A1 | 11/2012 | Hafezi et al. |
| 2012/0310070 A1 | 12/2012 | Kumar et al. |
| 2012/0316413 A1 | 12/2012 | Liu et al. |
| 2013/0030259 A1 | 1/2013 | Thomsen et al. |
| 2013/0057385 A1 | 3/2013 | Murakami et al. |
| 2013/0060115 A1 | 3/2013 | Gehman et al. |
| 2014/0334575 A1 | 11/2014 | Arne et al. |

FOREIGN PATENT DOCUMENTS

| | | |
|---|---|---|
| CN | 201076456 | 6/2008 |
| EP | 0344939 | 12/1989 |
| EP | 1246356 | 10/2002 |
| EP | 1342447 | 9/2003 |
| EP | 1534054 | 5/2005 |
| EP | 1702553 | 9/2006 |

(56) References Cited

FOREIGN PATENT DOCUMENTS

| | | |
|---|---|---|
| EP | 1789128 | 5/2007 |
| EP | 2143369 | 1/2010 |
| GB | 775071 | 5/1957 |
| GB | 2432862 | 6/2007 |
| IL | 172917 | 6/2010 |
| JP | 2000-506410 | 5/1912 |
| JP | 6117949 | 1/1986 |
| JP | 05-228128 | 9/1993 |
| JP | 09-330159 | 12/1997 |
| JP | 10-14898 | 1/1998 |
| JP | 2002-224053 | 8/2002 |
| JP | 2002263185 | 9/2002 |
| JP | 2002291684 | 10/2002 |
| JP | 3454525 | 10/2003 |
| JP | 2004-7187 | 1/2004 |
| JP | 2004-134384 | 4/2004 |
| JP | 2004-313242 | 11/2004 |
| JP | 2005-073886 | 3/2005 |
| JP | 2005-087552 | 4/2005 |
| JP | 2005-304880 | 4/2005 |
| JP | 2005124708 | 5/2005 |
| JP | 2005-532841 | 11/2005 |
| JP | 2005-532849 | 11/2005 |
| JP | 2006006377 | 1/2006 |
| JP | 2006509574 | 3/2006 |
| JP | 2006-177699 | 7/2006 |
| JP | 2006-187611 | 7/2006 |
| JP | 2006278091 | 10/2006 |
| JP | 2006346000 | 12/2006 |
| JP | 3876573 | 1/2007 |
| JP | 2007-159631 | 6/2007 |
| JP | 2007-313340 | 12/2007 |
| JP | 2007-330677 | 12/2007 |
| JP | 2008011865 | 1/2008 |
| JP | 2008501415 | 1/2008 |
| JP | 2008191955 | 8/2008 |
| JP | 2009-061236 | 3/2009 |
| KR | 20020015907 | 3/2002 |
| KR | 20020061744 | 7/2002 |
| KR | 200600977523 | 7/2006 |
| KR | 927471 | 11/2009 |
| KR | 10-2012-09995 | 9/2012 |
| TW | 553735 | 9/2003 |
| TW | 200724094 | 7/2007 |
| WO | WO8802237 | 4/1988 |
| WO | WO9221307 | 12/1992 |
| WO | WO9308734 | 5/1993 |
| WO | WO9319667 | 10/1993 |
| WO | WO9401165 | 1/1994 |
| WO | WO9516393 | 6/1995 |
| WO | WO9714112 | 4/1997 |
| WO | WO9739963 | 10/1997 |
| WO | WO9843537 | 10/1998 |
| WO | WO9937290 | 7/1999 |
| WO | WO9959465 | 11/1999 |
| WO | WO0033246 | 6/2000 |
| WO | WO0100085 | 1/2001 |
| WO | WO0147466 | 7/2001 |
| WO | WO0149364 | 7/2001 |
| WO | WO0174011 | 10/2001 |
| WO | WO0180731 | 11/2001 |
| WO | WO0235997 | 5/2002 |
| WO | WO0245489 | 6/2002 |
| WO | WO0258330 | 7/2002 |
| WO | WO0262276 | 8/2002 |
| WO | WO0287681 | 11/2002 |
| WO | WO0295351 | 11/2002 |
| WO | WO0305877 | 1/2003 |
| WO | WO0350643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005082436 | 9/2005 |
| WO | WO2005083621 | 9/2005 |
| WO | WO2005110238 | 11/2005 |
| WO | WO2005117697 | 12/2005 |
| WO | WO2006009404 | 1/2006 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006046648 | 5/2006 |
| WO | WO2006055892 | 5/2006 |
| WO | WO2006055956 | 5/2006 |
| WO | WO2006059338 | 6/2006 |
| WO | WO2006075016 | 7/2006 |
| WO | WO2006100620 | 9/2006 |
| WO | WO2006104843 | 10/2006 |
| WO | WO2006109072 | 10/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2008008281 | 1/2008 |
| WO | WO2008012700 | 1/2008 |
| WO | WO2008030482 | 3/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |

(56) References Cited

FOREIGN PATENT DOCUMENTS

| | | |
|---|---|---|
| WO | WO2009006615 | 1/2009 |
| WO | WO2009022343 | 2/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010115194 | 10/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |

OTHER PUBLICATIONS

Arshak et al., A Review and Adaptation of Methods of Object Tracking to Telemetry Capsules IC-Med; Jan. (2007) vol. 1, No. 1, Issue 1, 12pp.

"Asge Technology Status Evaluation Report: wireless capsule endoscopy" American Soc. For Gastrointestinal Endoscopy; Apr. (2006) vol. 63, No. 4; 7 pp.

Aydin et al., "Design and implementation considerations for an advanced wireless interface in miniaturized integrated sensor Microsystems" Sch. Of Eng. & Electron., Edinburgh Univ., UK; Sep. (2003); Abstract Only.

Barrie, Heidelberg pH capsule gastric analysis. Texbook of Natural Medicine, (1992), Pizzorno, Murray & Barrie.

Baskiyar, S. "A Real-time Fault Tolerant Intra-body Network" Dept. Of Comp. Sci & Soft Eng; Auburn University; Proceedings of the 27th Annual IEEE Conference; 0742-1303/02 (2002) IEEE; 6 pp.

Bohidar et al., "Dielectric Behavior of Gelatin Solutions and Gels" Colloid Polym Sci (1998) 276:81-86.

Brock, "Smart Medicine: the Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) pg. 91-96.

Delvaux et al., "Capsule endoscopy: Technique and indications" Clinical Gastoenterology; Oct. (2008) vol. 22, Issue 5, 1pp. (Abstract Only).

Dhar et al., "Electroless nickel plated contacts on porous silicon" Appl. Phys. Lett. 68 (10) pg. 1392-1393 (1996).

Eldek A., "Design of double dipole antenna with enhanced usable bandwidth for wideband phased array applications" Progress in Electromagnetics Research PIER 59, 1-15 (2006).

Evanczuk, S., "PIC MCU software library uses human body for secure communications link" ; EDN Network; edn.com; Retrieved from internet Jun. 19, 2013 at http://www.edn.com/electronics-products/other/4407842/Pic-Mcu-software-library-uses-human-body-for-secure-communications-link; Feb. 26 (2013); 5 pp.

Fawaz et al., "Enhanced Telemetry System using CP-QPSK Band—Pass Modulation Technique Suitable for Smart Pill Medical Application" IFIP IEEE Dubai Conference Apr. (2008); http://www.asic.fhoffenburg.de/downloads/ePille/IFIP_IEEE_Dubai_Conference.pdf.

Ferguson et al., "Dialectric Constant Studies III Aqueous Gelatin Solutions" J. Chem. Phys. 2, 94 (1934) pg. 94-98.

Furse C. M., "Dipole Antennas" J. Webster (ed). Wiley Encyclopedia of Electrical and Electronics Engineering (1999) pg. 575-581.

Gaglani S. "Put Your Phone, or Skin, on Vibrate" MedGadget; Mar. (2012) http://medgadget.com/2012/03/put-your-phone-or-skin-on-vibrate.html 8pp.

Gilson, D.R. "Molecular dynamics simulation of dipole interactions", Department of Physics, Hull University, Dec. (2002), pp. 1-43.

Given Imaging, "Agile Patency Brochure" (2006) http://www.inclino.no/documents/AgilePatencyBrochure_Global_GMB-0118-01.pdf; 4pp.

Gonzalez-Guillaumin et al., "Ingestible capsule for impedance and pH monitoring in the esophagus" IEEE Trans Biomed Eng; Dec. (2007) 54(12) 1pp. (Abstract Only).

Greene, "Edible RFID microchip monitor can tell if you take your medicine" Bloomberg Businessweek; Mar. (2010) 2 pp.; http://www.businessweek.com/idg/2010-03-31/edible-rfid-microchip-monitor-can-tell-ifyou-take-your-medicine.html.

Halthion Medical Technologies "Providing Ambulatory Medical Devices Which Monitor, Measure and Record" webpage. Online website: http://www.halthion.com/; downloaded May 30, (2012); 2 pp.

Heydari et al., "Analysis of the PLL jitter due to power/ground and substrate noise"; IEEE Transactions on Circuits and Systems (2004) 51(12): 2404-16.

Hoeksma, J. "New 'smart pill' to track adherence" E-Health-Insider; http://www.e-health-insider.com/news/5910/new_'smartpilLmonitors_medicines; May 17, 2010; 1pp.

Hoover et al., "Rx for health: Engineers design pill that signals it has been swallowed" University of Florida News; Mar. (2010) 2pp.; http://news.ufl.edu/2010/03/31/antenna-pill-2/.

Hotz "The Really Smart Phone" The Wall Street Journal, What They Know (2011); 6 pp.; http://online.wsj.com/article/SB10001424052748704547604576263261679848814.html?mod=djemTECH_t.

ISFET—Ion Sensitive Field-Effect Transistor; Microsens S.A. pdf document. First cited by Examiner in Office Action dated Jun. 13 (2011) for U.S. Appl. No. 12/238,345; 4pp.

Intromedic, MicroCam Innovative Capsule Endoscope Pamphlet. (2006) 8 pp (http://www.intromedic.com/en/product/productinfo.asp).

Jimbo et al., "Gastric-fluid-utilized micro battery for micro medical devices" The Sixth International Workshop on Micro and Nanotechnology for Power Geneartion and Energy Conservation Applications, (2006) pp. 97-100.

Jung, S. "Dissolvable 'Transient Electronics' Will Be Good for Your Body and the Environment" MedGadget; Oct. 1 (2012); Onlne website: http://medgadget.com/2012/10/dissolvabletransient-electronics-will-be-good-for-your-body-and-the-environment.html; downloaded Oct. 24, 2012; 4 pp.

Juvenile Diabetes Research Foundation International (JDRF), "Artificial Pancreas Project" Jun. (2010); http://www.artificialpancreasproject.com/; 3 pp.

Kamada K., "Electrophoretic deposition assisted by soluble anode" Materials Letters 57 (2003) 2348-2351.

Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. pp. 1-6.

Kim et al., "A Semi-Interpenetrating Network System for a Polymer Membrane"; Eur. Polym. J. vol. 33 No. 7; pp. 1009-1014 (1997).

Li, P-Y, et al. "An electrochemical intraocular drug delivery device", Sensors and Actuators A 143; pg. 41-48.; Jul. (2007).

Lifescan, "OneTouch UltraLink™" http://www.lifescan.com/products/meters/ultralink; Jul. (2010) 2 pp.

(56) References Cited

OTHER PUBLICATIONS

Lin et al., "Do Physiological Data Relate to Traditional Usability Indexes?" Proceedings of OZCHI 2005, Canberra, Australia (2005) 10 pp.
Mackay et al., "Radio Telemetering from within the Body Inside Information is Revealed by Tiny Transmitters that can be Swallowed or Implanted in Man or Animal" Science (1991) 1196-1202; 134; American Association for the Advancement of Science, Washington D.C.
Mackay et al., "Endoradiosonde" Nature, (1957) 1239-1240, 179 Nature Publishing Group.
Mandryk et al., "A physiological approach for continuously modeling user emotion in interactive play environments" Proceedings of Measuring Behavior (2008) (Maastrichtm the Netherlandsm Aug. 26-29) 2 pp.
Mandryk et al., "Objectively Evaluating Entertainment Technology" Simon Fraser University; CHI (2004) ACM 1-58113-703-6/04/0004; 2 pp.
Mckenzie et al., "Validation of a new telemetric core temperature monitor" J. Therm. Biol. (2004) 29(7-8):605-11.
Medtronic, "CareLink Therapy Management Software for Diabetes" Jul. (2010); https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® REAL-Time Revel™ System" Aug. (2010) http://www.medtronicdiabetes.com/products/index.html; 2 pp.
Medtronic, "MINI MED Paradigm® Revel™ Insulin Pump" Jul. (2010) http://www.medtronicdiabetes.com/products/insulinpumps/index.html; 2 pp.
Medtronic, Mini Med Paradigm™ Veo™ System: Factsheet (2010). http://www.medtronicdiabetes.com.au/downloads/Paradigm%20Veo%20Factsheet.pdf ; 4 pp.
Melanson, "Walkers swallow RFID pills for science" Engadget; Jul. (2008); http://www.engadget.com/2008/07/29/walkers-swallow-rfid-pills-for-science/.
Minimitter Co. Inc. "Actiheart" Traditional 510(k) Summary. Sep. 27 (2005).
Minimitter Co. Inc. Noninvasive technology to help your studies succeed. Mini Mitter.com Mar. 31 (2009).
Mini Mitter Co, Inc. 510(k) Premarket Notification Mini-Logger for Diagnostic Spirometer. Sep. 21 (1999).
Mini Mitter Co, Inc. 510(k) Premarket Notification for VitalSense. Apr. 22 (2004).
Minimitter Co. Inc. VitalSense Integrated Physiological Monitoring System. Product Description. Jul. (2005).
Minimitter Co. Inc. VitalSense Wireless Vital Signs Monitoring. Temperatures.com Mar. 31 (2009).
Mojaverian et al., "Estimation of gastric residence time of the Heidelberg capsule in humans: effect of varying food composition" Gastroenterology (1985) 89:(2): 392-7.
NPL_AntennaBasics.pdf, Radio Antennae, http://www.erikdeman.de/html/sail018h.htm; (2008) 3pp.
O'Brien et al., "The Production and Characterization of Chemically Reactive Porous Coatings of Zirconium Via Unbalanced Magnetron Sputtering" Surface and Coatings Technology (1996) 86-87; 200-206.
Owano, N., "Study proposes smart sutures with sensors for wounds" Phys.Org. Aug. (2012). http://phys.org/news/2012-08-smart-sutures-sensors-wounds.html; 2pp.
"PALO Bluetooth Baseband" PALO Bluetooth Resource Center; Retrieved from internet Dec. 12, 2012 at URL:http://palowireless.com/bluearticles/baseband.asp; first cited in Office Action dated Jan. 17, 2013 for EP08853901.0 (2013); 6pp.
Park, "Medtronic to Buy MiniMed for $3.7 Billion" (2001) HomeCare; http://homecaremag.com/mag/medical_medtronic_buy_minimed/; 2 pp.
Platt, D., "Modulation and Deviation" AE6EO, Foothills Amateur Radio Society; Oct. 26 (2007); 61 pp.

"RFID "pill" monitors marchers" RFID News; Jul. (2008) http://www.rfidnews.org/2008/07/23/rfidpill-monitors-marchers/.
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, pp. 2396-2407.
"SensiVida minimally invasive clinical systems" Investor Presentation Oct. (2009) 28pp; http://www.sensividamedtech.com/SensiVidaGeneralOctober09.pdf.
Shawgo, R.S. et al. "BioMEMS from drug delivery", Current Opinion in Solid State and Material Science 6; May (2002), pp. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20News letters.pdf; First cited in third party client search conducted by Patent Eagle Search May 18, 2010.
"Smartlife awarded patent for knitted transducer" Innovation in Textiles News: http://www.innovationintextiles.com/articles/208.php; 2pp. Aug. (2009).
"The SmartPill Wireless Motility Capsule" Smartpill, The Measure of GI Health; May (2010) http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", pp. 325-346 (2007).
Swedberg, "University Team Sees Ingestible RFID Tag as a Boon to Clinical Trials" RFID Journal (2010) Apr. 27; http://www.rfidjournal.com/article/view/7560/1 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. (1990), pp. 2005-2006.
Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.
Watson, et al., "Determination of the relationship between the pH and conductivity of gastric juice" Physiol Meas. 17 (1996) pp. 21-27.
Whipple, Fred L.; "Endoradiosonde," Nature, Jun. 1957, 1239-1240.
Winter, J. et al. "The material properties of gelatin gels"; USA Ballistic Research Laboratories, Mar. (1975), p. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the Internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using vol. Conduction of Biological Tissues" Proceedings of the 28th IEEE, EMBS Annual International Conference, Aug. 30-Sep. 3 (2006).
Zimmerman, "Personal Area Networks: Near-field intrabody communication" IBM Systems Journal (1996) 35 (3-4):609-17.

(56) References Cited

OTHER PUBLICATIONS

Description of ePatch Technology Platform for ECG and EMG, located it http://www.madebydelta.com/imported/images/DELTA_Web/documents/Me/ePatch_ECG_EMG.pdf, Dated Sep. 2, 2010.

Zworkin, "A Radio Pill" Nature, (1957) 898, 179 Nature Publishing Group.

* cited by examiner

RFID coils used Read ID's of IEM's as they fall through tube (RFID coils connected to electronics and informatics system)

Informatics system records container ID with ID's of each IEM

MULTI-MODE COMMUNICATION INGESTIBLE EVENT MARKERS AND SYSTEMS, AND METHODS OF USING THE SAME

CROSS-REFERENCE TO RELATED APPLICATION

This application is a continuation of U.S. patent application Ser. No. 13/888,190, filed on May 6, 2013, now U.S. Pat. No. 8,810,409, which is a continuation of U.S. patent application Ser. No. 13/564,479, filed on Aug. 1, 2012, now U.S. Pat. No. 8,542,123, which is a continuation of U.S. patent application Ser. No. 12/398,941, filed on Mar. 5, 2009, now U.S. Pat. No. 8,258,962 and, which pursuant to 35 U.S.C. §119(e), claims priority to the filing date of U.S. Provisional Patent Application Ser. No. 61/034,085 filed Mar. 5, 2008; the disclosure of which applications are incorporated herein by reference for all purposes.

INTRODUCTION

Healthcare concerns related to pharmaceutical products include supply chain issues, pharmacy errors and inefficiencies, unintentional disclosures of information related to patients and/or medications, and patient error and misuse of medication. There remains a long-standing need for a safe, cost-effective, comprehensive solution to safeguard medication and protect patients from the consequences of these issues surrounding medications.

SUMMARY

Aspects of the invention include multi-mode communication ingestible event marker devices. The multi-mode communication ingestible event marker devices include an ingestible component comprising an integrated circuit comprising a conductive communication module; and at least a second non-conductive communication module, which may be associated with the ingestible component or a packaging component thereof. The communications modules can include antennas, integrated circuitry, and/or related components, in various combinations and configurations. Various configurations of the communications unit combine or separate components making up the communications modules, such as antennas, power sources, or integrated circuitry, to achieve a range of design objectives. Further, the devices can communicate with various other devices, including transmitters/receivers associated with inventory control, pharmacy control, and inter- and intra-body devices.

Additional aspects of the invention include systems that can be used across multiple and varied applications to provide various benefits across the duration of an ingestible event marker's existence. For example, systems of the invention may provide inventory control information related to medication manufacturing and packaging management operations as well as supply chain control. Systems of the invention may also provide pharmacy-related quality control measures and personalization applications related to medication, medications packaging, and patient history. Systems of the invention may also provide patient safety information as well as safety control measures. Some systems of the invention may provide and/or suppress data associated with the system in accordance with preset or dynamically updatable control functions.

Accordingly, aspects of the invention include devices comprising an ingestible component comprising an integrated circuit comprising a conductive communication module; and a second non-conductive communication module. The second non-conductive communication module comprises, in some instances, at least one module selected from the group consisting of a wireless radio-frequency module, a magnetic induction module, an optical module, an acoustic module, and a wired module. In some instances, the non-conductive communication module is a wireless radio-frequency module that comprises a radio-frequency identification module. In other instances, the non-conductive communication module may be an infrared frequency module. The ingestible component may include a power source, such as a power source made up of a pair of electrodes fabricated from dissimilar materials. Ingestible event marker devices may also include a second power source electrically coupled to the non-conductive communication module, such as a coil, e.g., an RFID coil. In some instances, the ingestible component comprises the non-conductive communication module. In such instances, the non-conductive communication module may be electrically coupled to the integrated circuit of the ingestible component, i.e., the ingestible component integrated circuit. In such instances, the ingestible component integrated circuit, conductive communication module and at least a portion of the non-conductive communication module may be integrated into an ingestible event marker identifier component. In some instances, the non-conductive communication module comprises a non-conductive transmitter, such as an RF antenna, e.g., an RF antenna coil, which may be associated with the ingestible component, such as with a skirt component, or may be associated with a packaging component of the device. In some instances, the non-conductive communication module is electrically coupled to a second integrated circuit that is distinct from the ingestible component integrated circuit. When present, this second integrated circuit and ingestible component integrated circuit may be configured to communicate with each other. In some instances, at least a portion of the non-conductive communication module is configured to be separable from the ingestible component in a manner that does not compromise the function of the conductive communication module. The ingestible component may include an active pharmaceutical agent, which agent may be present in a physiologically acceptable vehicle and/or a skirt component of an ingestible event marker. The physiologically acceptable vehicle may be configured as a tablet or capsule in some instances.

Additional aspects of the invention include systems that comprise: an ingestible component comprising an integrated circuit comprising a conductive communication module configured to emit a first signal; a second non-conductive communication module configured to emit a second signal; and a receiver. In these systems, the receiver, conductive communication module and non-conductive communication module may be configured to provide for transmission of information between the receiver and at least one of the conductive communication module and the non-conductive communication module. In some instances, the receiver is configured to receive at least one of the first signal and the second signal. Any of the first and second signals may be encrypted as desired, for example by using any convenient cryptographic protocol. Where the receiver is configured to receive the second signal, in some instances the receiver comprises a radio-frequency reader. As desired, the receiver may be configured transmit information to the non-conductive communication module. In some instances of the systems, the receiver is a component chosen from a system selected from the group consisting of manufacturing systems, supply chain management systems and health care management (such as pharmacy) systems. Manufacturing system components which may include a receiver as described herein include sorters, programmers, encoders, etc. Supply chain management system components which may include a receiver as described herein include trackers and programmers. Health care management system components which may include a receiver as described herein include scanners, encoders, and the like. In some instances, the receiver of the system is configured to the first signal, which first signal may comprise non-physiologic data. The receiver may be configured to removably attached to a living being, e.g., via an adhesive component. Alternatively, the receiver may be an implantable receiver. Where desired, the implantable receiver may include additional functionality, such as electrical stimulation functionality, physiological data measurement functionality, etc.

Aspects of the invention further include various methods, such as methods of detecting at least one of a first signal and a second signal from a device comprising that includes an ingestible component comprising an integrated circuit comprising a conductive communication module configured to emit the first signal; and at least a portion of second non-conductive communication module configured to emit the second signal. The methods may include detecting only the first or second signal, or both the first and second signal. Additional methods include emitting at least one of a first signal or a second signal from a device comprising that includes an ingestible component comprising an integrated circuit comprising a conductive communication module configured to emit the first signal; and at least a portion of second non-conductive communication module configured to emit the second signal. The methods may include emitting only the first or second signal, or both the first and second signal.

Additional methods of the invention includes methods of transmitting a signal between a non-conductive communication module and a receiver, wherein the non-conductive communication module is a component of a device that includes an ingestible component comprising an integrated circuit comprising a conductive communication module; and the second non-conductive communication module. In such methods, the receiver may be a component chosen from a system selected from the group consisting of manufacturing systems, supply chain management systems and health care management systems. Where the receiver is a component of a manufacturing system, the manufacturing system may be a high-throughput manufacturing system. Regardless of whether the receiver is a component of a manufacturing system, supply chain management system or health care management system, the signal may be transmitted from the device to the receiver and/or from the receiver to the device.

Additional methods of the invention include methods of administering to a subject a device comprising an ingestible component comprising an integrated circuit comprising a conductive communication module configured to emit the first signal; and at least a portion of second non-conductive communication module configured to emit the second signal. These methods may include receiving the first signal at a receiver and may further include determining historical information (such as pedigree information) for the ingestible component from the received first signal.

In some instances, the term "Lifecycle" is employed to refer to devices and systems of the invention. "Lifecycle" encompasses the time during which a pharmaceutical product exists, extending from manufacture through destruction. This period includes, for example, medication manufacture, supply chain management, pharmacy management, and patient possession. Lifecycle can also refer to a single phase of the pharmaceutical product existence, or select multiple phases of its existence.

"Pharma Informatics" and "medication data" refer to information regarding medication and its use, including information relating to manufacture, supply chain, pharmacy inventory and distribution, patient identifying data, dosage directions, and consumption data. For example, information used by the system can include the date, time, and location of manufacture, batch number, lot number, medication name, medication type, manufacturer name, pharmacy name, date and time of transfer from pharmacy to patient, time of ingestion, and time of expulsion.

Aspects of RFID systems used for pharmaceutical tracking as discussed in published United States Patent Application Nos. 2007/0008112, 2006/0061472 and 2005/0285732 can also be used in the systems and are hereby incorporated by reference in their entirety.

DETAILED DESCRIPTION

Figure 1A:
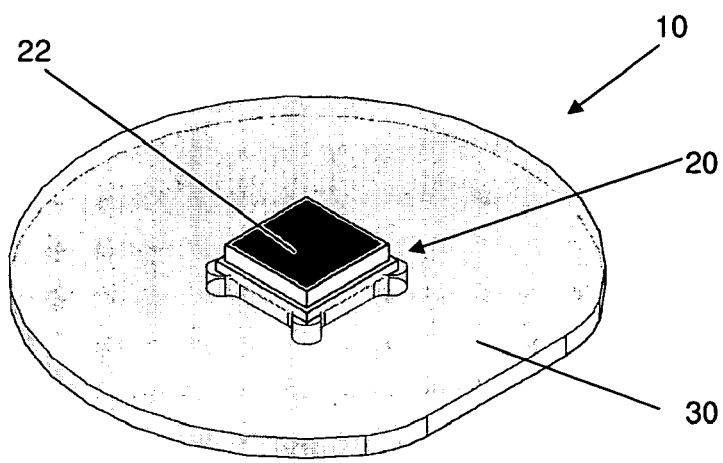
FIGS. 1A to 1B shows an ingestible event marker identifier according to one embodiment.

As summarized above, aspects of the invention include multi-mode communication ingestible event marker devices. Ingestible event marker devices of the invention include an ingestible component comprising a conductive communication module and at least one additional non-conductive communication module. The non-conductive communication module may be integrated with the ingestible component or at least a portion or all of the non-conductive communication module may be associated with a packaging component of the ingestible event marker device. Systems of the invention that include the ingestible event marker devices and a receiver may be configured to provide medication information and control measures across the entire life cycle of the ingestible event marker. The life cycle includes, for example, medication manufacture, supply chain management, pharmacy management, and patient use management.

Ingestible event marker devices of some embodiments may include an ingestible component that includes an integrated circuit component comprising a conductive communication module (for example present as an integrated identifier) and at least a second non-conductive communication module, where the number of additional non-conductive communication modules may vary, for example one or more, two or more, three or more, etc. Accordingly, the ingestible event marker devices of the invention may be viewed as multi-mode communication ingestible event marker devices, since they include at least two distinct communication modules, one of which is a conductive communication module. As indicated above, the at least second non-conductive communication module may be associated with the ingestible component or partially or wholly associated with a packaging component of the device, if present. As such, ingestible event marker devices of the invention may or may not include packaging associated with the ingestible component, where packaging may be configured in a variety of different formats, such as blister packs, multi-dose containers, and the like. In some instances, the communications modules are dynamically combined with medication components (when present) to achieve highly effective and accurate information and control solutions in a viable, cost-effective manner. For example, in one embodiment, the communications modules are implemented as an integral part of a pill and/or medication packaging. Further, the systems can communicate with various other devices, including transmitters/receivers associated with inventory control, pharmacy control, and inter- and intra-body devices.

As summarized above, the devices and systems of the invention include at least one non-conductive communication module. By non-conductive communication module is meant a communication module that communicates using a communications protocol other than a conductive communication protocol which uses body fluid as a conduction medium (for example, as further described in PCT Published Application Publication Nos. WO 2006/116718; WO 2008/008281; WO 2008/095183 and WO 2008/063626; the disclosures of which are herein incorporated by reference). Non-conductive communication protocols, i.e., modes, of interest include, but are not limited to: wireless radio-frequency modes; magnetic induction modes; optical modes, such as infra-red frequency optical modes; acoustic modes; as well as wired modes, i.e., direct modes. Accordingly, in some instances the non-conductive communication module may be at least one module selected from the group consisting of a wireless radio-frequency module, a magnetic induction module, an optical module, an acoustic module, and a wired module.

In some embodiments of interest, the non-conductive communication module is a wireless radio-frequency module. While the wireless radio-frequency communication module may vary, in some instances this module is a radio-frequency identification (RFID) module. For ease of description purposes only, embodiments of the invention will now be further described in terms of embodiments where the non-conductive communication module is an RFID communication module. However, as noted above the non-conductive communication module may vary widely.

In some instances, the RFID module incorporates, for example, an integrated circuit and an RF antenna. The RFID module may be communicatively associated with a conductive module incorporating, for example, an integrated circuit and a conductive antenna. Either of the RFID module or the conductive module, or both, may function in conjunction with medication and/or medication packaging to receive, process, store, and/or transmit information related to or associated with the medication. As indicated above, the devices and systems can be used across multiple and varied applications to provide secure, controlled, and accurate communications in viable, cost-effective implementations.

Broadly, the devices and systems facilitate information communication and control measures up to the entire life cycle of an ingestible event marker. The systems are capable of application in a variety of communications environments, particularly in environments where wireless communications are preferred. For example, the communications environments include inventory control environments as well as inter-body and intra-body communications.

Inter-body and intra-body communications include, for example, active, passive, and semi-passive systems associated with data transmission and reception from implantable, ingestible, insertable, and attachable medical devices and medications associated with the human body or other living organisms. The medical devices are capable of communication and/or integration with systems of the invention.

As reviewed above, the ingestible event marker devices of the invention include an ingestible component that comprises at least an integrated circuit and a conductive communications module. This structure is collectively referred to herein as an ingestible event marker, and ingestible event markers may or may not include additional components, such as a physiologically acceptable vehicle and/or an pharmaceutically active agent. Accordingly, the ingestible event markers described herein, sometimes referred to herein as "IEMs", at least include an ingestible component that includes an integrated circuit that comprises a conductive communication module, where the conductive communication module includes a conductive transmitter. The integrated circuit and conductive communication module may be collectively referred to as an identifier. Identifiers of interest are structures that generate (for example emit) a detectable signal upon contact of the ingestible event marker identifier with a target physiological location (or locations). The ingestible event marker identifiers may vary depending on the particular embodiment and intended application of the composition, as long as they are activated (turned on) upon contact with a target physiological location, such as the stomach or small intestine. As such, an ingestible event marker identifier may be a structure that emits a signal when activated at a target site, for example when it contacts a target body site. The ingestible event marker identifier may be any component or device that is capable of providing a detectable signal following activation. Ingestible event marker identifiers according to embodiments of the invention include a signal generation component. The ingestible event marker identifier may be configured to emit a signal once the composition comes into contact with a physiological target site. Depending on the embodiment, the target physiological site or location may vary, where representative target physiological sites of interest include, but are not limited to: a location in the gastrointestinal tract, such as the mouth, esophagus, stomach, small intestine, large intestine, etc. Ingestible event marker identifiers may be configured to be activated upon contact with fluid at the target site, e.g., stomach fluid, regardless of the particular composition of the target site. Where desired, the ingestible event marker identifier may be configured to be activated by interrogation, following contact of the composition with a target physiological site. The ingestible event marker identifier may be configured to be activated at a target site, where the target site is reached after a specified period of time.

Depending on the needs of a particular application, the signal obtained from the ingestible event marker identifier may be a generic signal, such that the signal is a signal that merely identifies that the composition has contacted the target site. Alternatively, the signal may be a unique signal, such as a signal which in some way uniquely identifies that a particular ingestible event marker from a group or plurality of different ingestible event markers, for example a batch of ingestible event markers, has contacted a target physiological site. As such, the ingestible event marker identifier may be one that emits a signal that cannot be distinguished from the signal emitted by the ingestible event marker identifier of any other ingestible event marker member of a batch from which the ingestible event markers are obtained. Alternatively, each ingestible event marker member of a batch of ingestible event markers may have an ingestible event marker identifier that emits a unique signal, at least with respect to all of the other ingestible event marker identifiers of the ingestible event marker members of the batch. The ingestible event marker identifier may emit a unique signal that is a universally unique signal (where such a signal may be analogous to a human fingerprint which is distinct from any other fingerprint of any other individual and therefore uniquely identifies an individual on a universal level). The signal may either directly convey information about a given event, or provide an identifying code, which may be used to retrieve information about the event from a database, such as a database linking identifying codes with compositions. Where desired, the signal may be encrypted in a manner that provides control over access to the signal and informational content thereof.

The ingestible event marker identifier at least generates a conductive (near field) signals, which signal is one that is communicated via a conductive communication protocol that uses body fluid as a conduction medium (for example, as further described in PCT Published Application Publication Nos. WO 2006/116718; WO 2008/008281; WO 2008/095183 and WO 2008/063626; the disclosures of which are herein incorporated by reference). Depending on the given embodiment, the ingestible event marker identifier may transmit a given signal once. Alternatively, the ingestible event marker identifier may be configured transmit a signal with the same information (identical signals), two or more times, where the collection of discrete identical signals may be collectively referred to as a redundant signal.

The ingestible event marker identifiers may vary depending on the particular embodiment and intended application of the composition so long as they are activated upon contact with a target physiological location, such as the stomach. Ingestible event marker identifiers may include an activation component, such as a battery that is completed by stomach acid, and a transmission element. In these embodiments, the identifier may be viewed as including a "wet battery" power source, which power source at least provides power to the conductive communication module, and may or may not provide power to the non-conductive communication module, as further developed below. Examples of different types of ingestible event marker identifiers of interest include, but are not limited to, those ingestible event marker identifiers described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753; the disclosures of which are herein incorporated by reference.

Figure 1B:
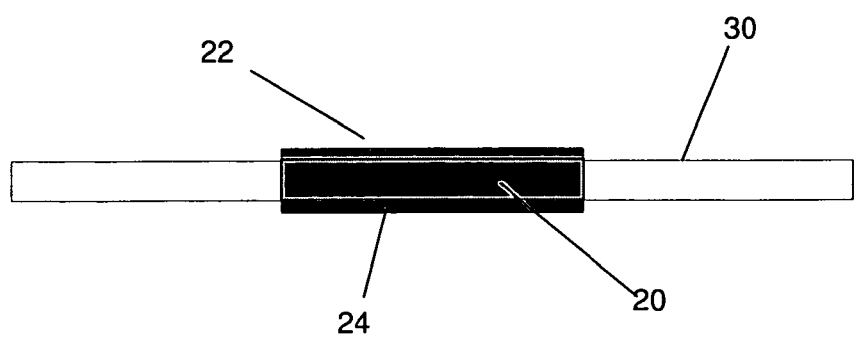

An example of an ingestible event marker of interest is depicted in FIGS. 1A and 1B. The ingestible event marker 10 shown in FIGS. 1A and 1B includes an integrated circuit component 20 (also referred to herein as the identifier) as well as upper and lower electrodes 22 and 24, where the upper and lower electrodes are fabricated from dissimilar materials and are configured such that upon contact with stomach fluid current runs through the integrated circuit to cause one or more functional blocks in the circuit to emit a detectable signal. The marker shown in FIGS. 1A and 1B includes a virtual dipole signal amplification element 30 (sometimes referred to herein as a "skirt"), as reviewed in greater detail in PCT application serial no. PCT/US20008/077753, the disclosure of which is herein incorporated by reference.

In one example, the IEM includes a conductive antenna, a conductive modulator, and a wet battery. The digestive system liquids, for example, activate the battery, which acts as a power source for various Ingestible Event Marker components. Detection events occur via liquid contact. Data is transmitted via the conductive antenna to a receiving device.

The ingestible event marker devices may be used in conjunction with receivers configured to receive the conductive signal emitted by the conductive communication module of the ingestible event maker. One example of an attachable medical device is a transmitter/receiver (which may be referred to herein as a Raisin receiver), permanently associated with a body (such as implanted in a body) or removably attachable to an external portion of a body. Receivers of interest include, but are not limited to, those receivers configured to detect a conductively transmitted signal described in PCT Published Application Publication Nos. WO 2006/116718; WO 2008/008281; WO 2008/095183 and WO 2008/063626; the disclosures of which are herein incorporated by reference. As such, the IEM can be communicably associated with a transmitting and/or receiving device such as the Raisin, supra. The transmitting/receiving device includes in-body devices, external devices removably or permanently attachable to the body, and remote devices, i.e., devices not physically associated with the body, but capable of communication with the Ingestible Event Marker.

Various embodiments of the devices and systems, including communication-enabled pills and packaging, enable identification of the IEM and any medication thereof (if present). "Pill" as used below is representative of any communication-enabled medication. IEM packaging includes, for example, a "blister" pack capable of housing an individual IEM (such as a pill or a limited number of pills or capsules). The IEM packaging further includes containers, boxes, wrappings, IV bags, and so forth associated with the medication.

In various embodiments, the communication components can be sovereign to the pill. In other embodiments, the communication components can be distributed, e.g., the RF module or portions thereof are physically associated with the packaging and the conductive communications module is physically associated with the ingestible component, such as a pill or capsule. For example, RFID communications can be terminated when the pill is removed from the packaging due to the physical severance of RFID module components from the remainder of the device. In one embodiment, the RFID antenna is located on the medication packaging and is separated from the remainder of the device via a "snap-off" mechanism, thus preventing RF communications with the ingestible component once it has been removed from its packaging. In another embodiment, the RFID antenna is removed at the time the pharmacy delivers IEM to the patient. In the above examples, other RFID module components, such as a data storage component, can be associated with the RF antenna in such a way that they are separated from the remainder of the system along with the antenna. Alternatively, the RF antenna could remain attached to the pill while another part of the RFID module is separated from the pill. As such, in some instances at least a portion of the non-conductive communication module is configured to be separable from the ingestible component in a manner that does not compromise the function of the conductive communication module. One advantage of separating part or all of the RFID module from the conductive communications module in this manner is the patient privacy protection afforded by termination of RFID communications.

In some embodiments, some or all of the data readable on or written to the RFID system will be removable via severance of the RFID module from the conductive module to protect patient privacy. However, in other embodiments, retention of such data after separation could be desirable for long term tracking and/or identification purposes.

The RFID components can be used to encode the pill or the medication packaging with various data such as medication identification information, dosage information, lot and batch numbers, and expiration dates. These data can be manipulated in any manner to optimize functionality. For example, quality control processes can read each IEM's information and aggregate the information consistent with optimal inventory, shipping tracking, and financial processes. Automated sorters can communicate with each IEM to efficiently process, sort, and package medications.

Similarly, shipping operations can be tracked and controlled to ensure positive medication identification, medication location, and so forth. In one example, once medication distribution has commenced, the device and system can be used to check for counterfeit medications, such as might be received from international points or from other locations lacking good regulatory practices.

Pharmacy operations can be optimized with use of the devices and systems. For example, upon receipt of medications into the pharmacy, the staff can scan the medication packaging and the medications to ensure receipt of the expected products and authenticity of the medication. Prior to dispensing the medication to a patient, the pharmacy can encode the medication packaging, containers, and individual medications with patient-pertinent information. For example, such information includes patient identification, medication identification and patient-specific dosage and expiration information. Further information includes contraindicated medications, warnings, and so forth. In this manner, the history, traceability, efficacy and safety of the medication are addressed.

In addition, various embodiments of the devices can interoperate with dispensing devices in systems of interest. For example, once medication information is read into the system, the dispensing device aggregates various medications into a container or even a single IEM or formulation for a particular patient.

In various embodiments, the device can be a very small, low range unit. A very strong RF detector, such as an RFID wand or a gate that individual pills pass through, e.g., a funnel as depicted in certain of the figures, can be used to communicate with the device outside the body, for example, within a range of 100 μm to ten meters, such as 3 μm to 3 centimeters, e.g. approximately 1 centimeter. Once ingested, however, the low range of the RFID communication module does not facilitate communication with random devices, i.e., those not intended or authorized to communicate with the IEM. In this manner, privacy concerns regarding unauthorized or unintentional communication of information associated with the IEM are minimized. Higher range RFID devices i.e., functioning with in a range of one meter to 20 meters, such as one meter to three meters, e.g. 2 meters, may be employed for some tracking applications. In this application, privacy protection can be provided by separation of RFID and conductive communications modules as described above. Alternatively, privacy may be provided in this and any particular communication by employing suitable encryption techniques, such that any signal of interest where privacy considerations are of concern is encrypted. Any convenient encryption protocol may be employed.

The frequency range in which the RFID module operates can also be selected to achieve various design goals. Low frequency RF, i.e. radio waves in the Hz/kHz range, for example, between 5 kHz and 500 kHz, such as 125 kHz, may be preferable for communications while the device is in use by the patient. However MHz/GHz range RF, e.g. in the range of 1 MHz to 1 GHz, such as 13.56 MHz, can facilitate tracking of the system prior to patient use. Multiple RFID modules can be combined within one system to facilitate these different needs.

Once the IEM reaches the patient environment, information associated with the IEM can be used for a variety of purposes. For example, the IEM may interoperate with the IEM container and with a receiver such as the Raisin, supra, to ensure that the person attempting to open the IEM container is actually the person for whom it is prescribed. Further communication activities include an information control system, in which medication information associated with the IEM device is compared against patient data received from one or multiple sources to determine, for example, if a medication is contraindicated, subject to appropriate dosage amounts and times, or other events and/or conditions.

After patient ingestion, information stored by the IEM may be recovered from one or more of the communications modules. For example, communication capabilities can be performed after ingestion via the conductive communication components, for example, using the Ingestible Event Marker and a Raisin receiver. In some embodiments, a device with a limited RF range maintains patient privacy respecting to information stored by the system. Other embodiments of the system provide for separation of RFID module components to prevent RF access to the device.

Data can be stored in the device and reprogrammed with secure digital signature at each transaction.

When patient expulsion of a IEM has taken place, various embodiments permit communication with a device such as a sensor to determine, for example, data related to the patient or the medication, or transit time through the body. Alternatively, in various embodiments, the data is erased (or various components/subcomponents associated with the data are destroyed or separated from the system) to protect privacy concerns after expulsion.

Figure 2:
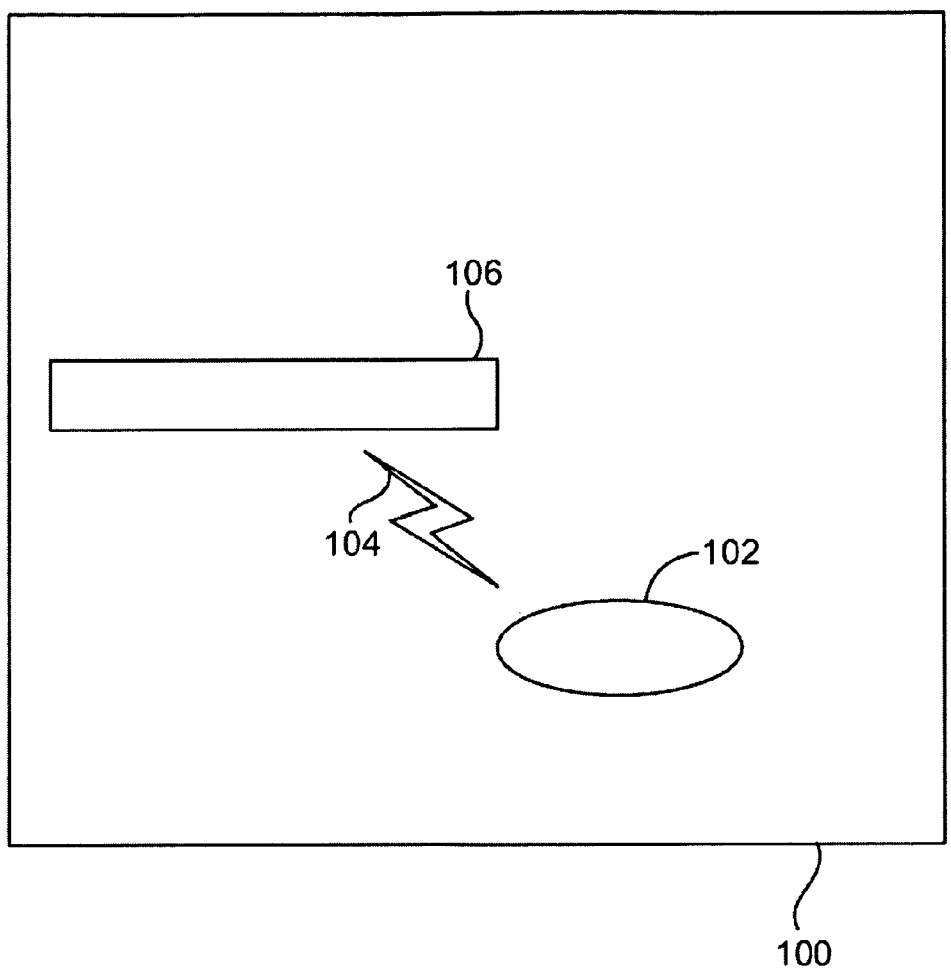
FIG. 2 shows a communications environment according to one embodiment.

In FIG. 2, there is shown a communications environment 100 including an ingestible event marker device 102, according to one embodiment, which includes both a conductive communication module and an RFID module. The RFID module of the device 102 interacts via a communication link 104 with a receiver configured to receive a signal from at least one of the conductive communication module or RFID communication module of the device. For example, receiver 106 may be an RFID wand 106. In communication environment 100, the device 102 interacts with, e.g., brings in power from, the RFID wand 106. The RFID wand 106, for example, operates on a radio frequency and transmits data to and/or receives data from the device 102. In this manner, communication can be achieved without reliance on liquid contact to activate a power source. In addition, in certain embodiments, the device 102 is powered by the radio signal of the associated communication device, e.g., RFID wand 106. In this manner, the device 102 provides a relatively small size overall to facilitate ease of ingestion, implantation, maintenance, and traversal activities related to the body.

Figure 3:
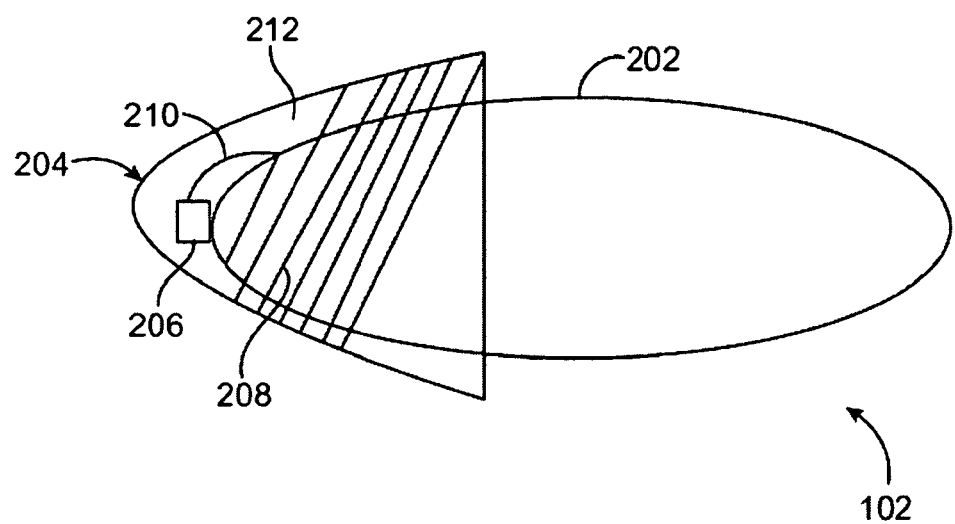
FIG. 3 shows the system of FIG. 2, according to one embodiment.

More particularly, FIG. 3 shows the ingestible event marker device 102 of FIG. 1, according to one embodiment. The device 102 includes a pill 202 and a communications module 204. The communications module includes an integrated circuit ("chip") 206, an RF antenna 208, lead(s) 210, and an antenna skirt 212. The pill 202 may have various pharmaceutical configurations, such capsules, caplets, gel caps, solid pills, tablets, and other types of pill medications. The pill 202 may include a physiologically acceptable vehicle, and may or may not further include a pharmaceutically active agent. The chip 206 is permanently or removably affixed to, or integrated with, at least a portion of the pill 202. The chip 206 includes various combinations of components/subcomponents (not shown). For example, the chip 206 can include or be otherwise associated with a memory, a processor, a storage unit, a transmitter and/or receiver, or other components associated with data processing, storage, transmission, and receipt.

The RF antenna 208 permanently or removably attaches to, or is otherwise in communication with, the chip 206 via leads 210. In various embodiments, the antenna 210 is integrated, or otherwise associated with, the antenna skirt 212 (also referred to above as a virtual-dipole signal amplifier). In various embodiments, the antenna skirt 212 can be flexible, inflexible, foldable, unfoldable, rollable, unrollable, expandable or otherwise manipulated. In this manner, the folded antenna skirt 212 facilitates ingestion/implantation, yet expands in the body to promote communication transmittal and reception. The antenna skirt can be implemented in various materials or combinations of materials, so long as the functionality described herein is carried out.

Figure 4:
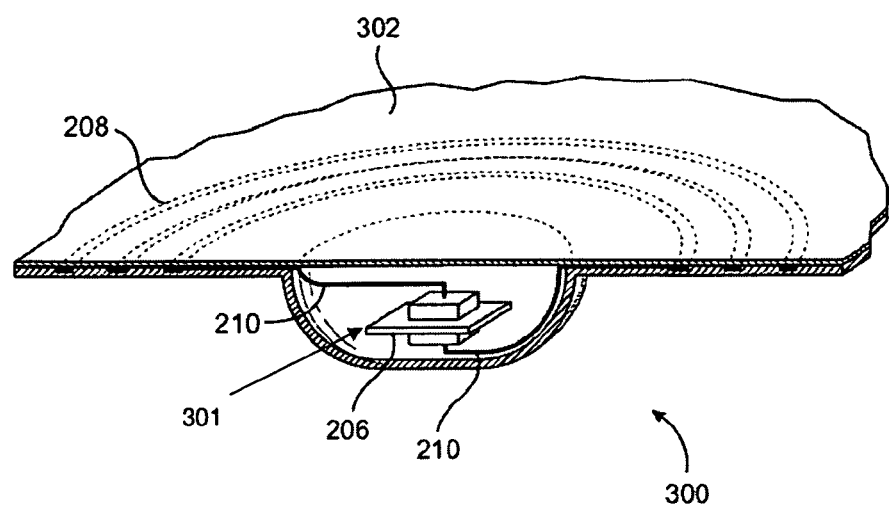
FIG. 4 shows a cross-sectional view of a system according to another embodiment.

FIG. 4 shows a cross-sectional view of an ingestible event marker device 300, according to another embodiment. The ingestible event marker 300 includes packaging 302, such as a "blister" pack. Chip 206 of device 300 includes an RFID communication module electrically coupled to the RF antenna 208 via the leads 210. The RF antenna 208 can be integrated into or formed in any manner associated with the packaging 302. The chip 206 can be located or associated with either the blister pack, e.g., where separate communicably associated chips can be attached to the blister pack and the pill. Alternatively, chip 206 may be part of an ingestible component (not shown) such as a pill, such as where chip 206 further includes a conductive communication module. Communication associated with the blister pack can be achieved without having all of the RFID components onboard an ingestible component, thus providing an alternative to ingestion of the entire RFID communication. Therefore, the RFID off-board components, i.e., components not physically associated with the ingestible component, need not consist of edible materials.

Figure 5:
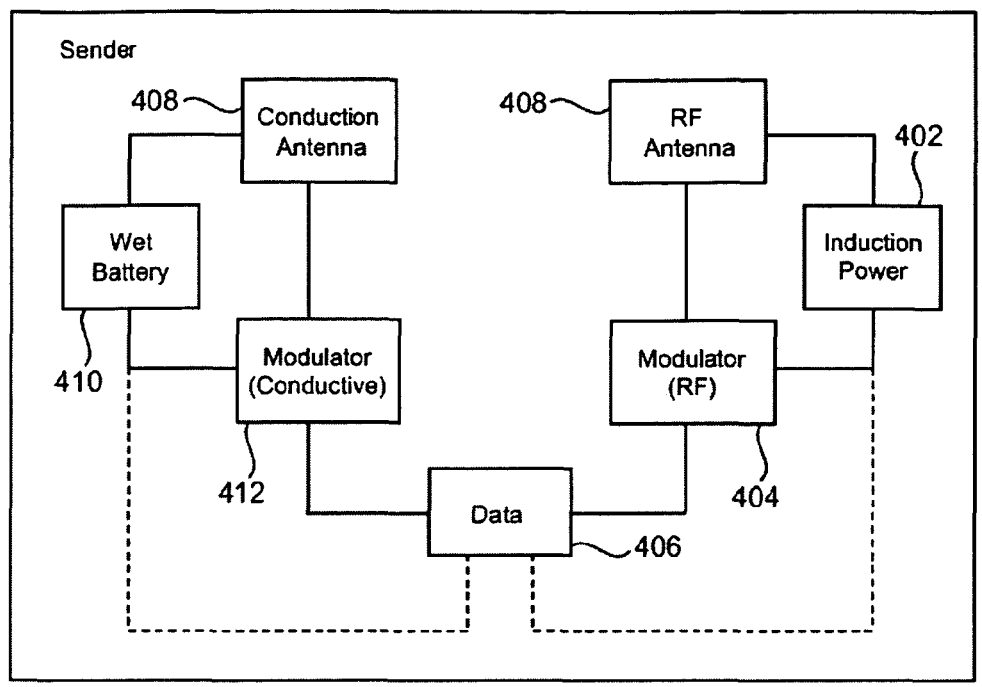
FIG. 5 shows a schematic of a first pill communication system, according to one embodiment.

As illustrated below, an RFID communication module 204 may be associated to varying degrees with conductive components of an IEM. For example, FIG. 5 shows a schematic of a first pill communication system 400, sometimes referred to as a "sender", including the RF antenna 208 powered by an induction power source 402. The induction power source 402 includes, for example, the RFID wand 106 (shown in FIG. 2). The RF antenna 208 is communicably associated with a first modulator 404, which modulates a signal associated with data 406, which can be stored, for example, in a memory (not shown) or other media.

The pill communication system 400 further includes a conductive antenna 408 powered by a wet battery 410. The wet battery 410 is activated, for example, by digestive liquids. The conductive antenna 408 is communicably associated with a second modulator 412, which modulates a signal associated with the conductive antenna 408. The second modulator 412 is communicably associated with data 406, which can be associated, for example, in a memory (not shown) or other media. In this manner, common data, e.g. data 406 can be transmitted via two different links, depending on the desired functionality.

For example, data can be modulated and transmitted via the RF antenna 208 during manufacturing, shipping, pharmacy, and home operations. The same (or different) data can be transmitted via the conductive antenna 408 after ingestion of the pill. In various embodiments, after expulsion from the body, a time of expulsion can be determined and used, for example, to calculate a total transmittal time through the body.

In some embodiments, some or all of the data stored on the system can be erased, destroyed, etc. For example, the pill includes fusible links (not shown) and use a portion of the power to completely erase data from memory or physically destroy memory. For example, when the conductive communication module power source, e.g. wet battery, is activated, the power provided triggers data deletion. In this manner, if the pill is recovered there is no data to be retrieved by unauthorized sources and the patient's privacy interests are preserved. Separating the data into separate modules (not shown) further allows a portion of stored data to be deleted, e.g. patient or dosage information, while allowing a portion of the data to remain, e.g. medication identifying information.

A further advantage offered by separation between portions of the RFID communications module and the conductive communications module is a failsafe mechanism for obtaining data stored on the pill. That is, if one communications module fails, the other module remains available to facilitate communications. For example, if one or more components of the conductive communications module cease to function, an RFID wand 106 (shown in FIG. 2) could be used to power the pill communication system 400 inductively to obtain information from data 406.

Moreover, separating the conductive communication module from the RFID communication module components facilitates physical disabling of a part of the system via a "snap-off" mechanism as described supra.

Figure 6:
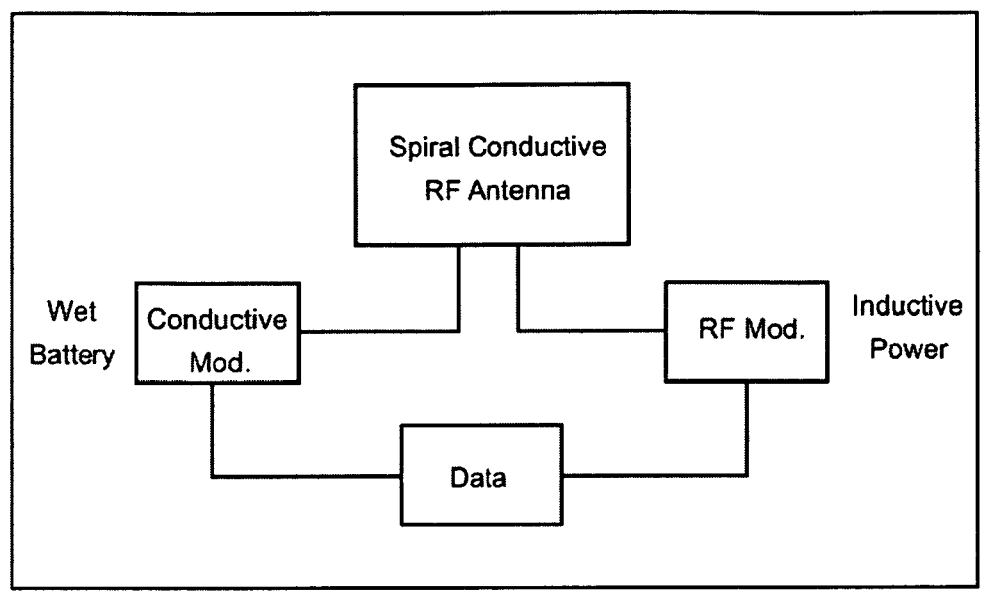
FIG. 6 shows a schematic of a second pill communication system, according to one embodiment.

FIG. 6 shows a schematic of a second pill communication system 500, according to one embodiment. The second pill communication system includes a spiral conductive RF antenna 502, an RF modulator 404, a conductive modulator 412 and data 406. The antenna is communicably associated with an RF modulator 404 powered by an induction power source. The RF modulator 404 modulates a signal associated with the antenna. The RF modulator 404 is communicably associated with data 406, which can be associated, for example, in a memory (not shown) or other media. The antenna 502 is further communicably associated with a conductive modulator 412 powered by, e.g., a wet battery. The conductive modulator modulates a signal associated with the antenna. The conductive modulator is communicably associated with data 406, which can be associated, for example, in a memory (not shown) or other media. In this manner, the second pill communication system accommodates both conductive and RF modulation of signals associated with a single antenna. An IEM device featuring a single antenna which facilitates both conductive and RF communications would potentially reduce the component, design, and test costs associated with the complete system. Moreover, the modes of failure are reduced as components are removed from the system. The potential for antenna failure is reduced when the system includes one antenna rather than two.

Figure 7:
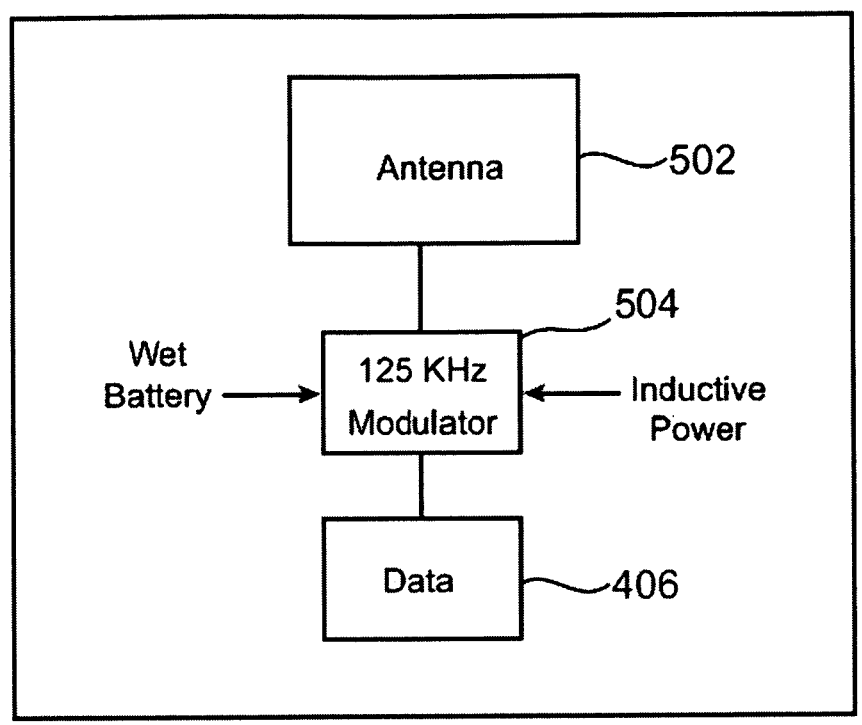
FIG. 7 shows a schematic of a third pill communication system, according to one embodiment.

FIG. 7 shows a schematic of a third pill communication system 600, according to one embodiment. The third pill communication system 600 includes an antenna 502, a modulator 602, and data 406. The modulator 602 modulates a signal from the antenna 502 and can be powered by one or more sources, e.g., a wet battery and/or an inductive power source. In one embodiment, for example, the modulator 504 is a 125 Kilohertz (KHz) modulator. In other examples, the modulator is a 13 Megahertz (MHz) modulator or other frequency bands. In this manner, the second pill communication system 500 accommodates both inductive and conductive power sources in a single modulator/antenna design, permitting multiple types of communication in multiple communication environments. The advantages of component integration as illustrated in FIG. 5, supra, are further realized with further reduction of the number of components in the system.

Figure 8A:
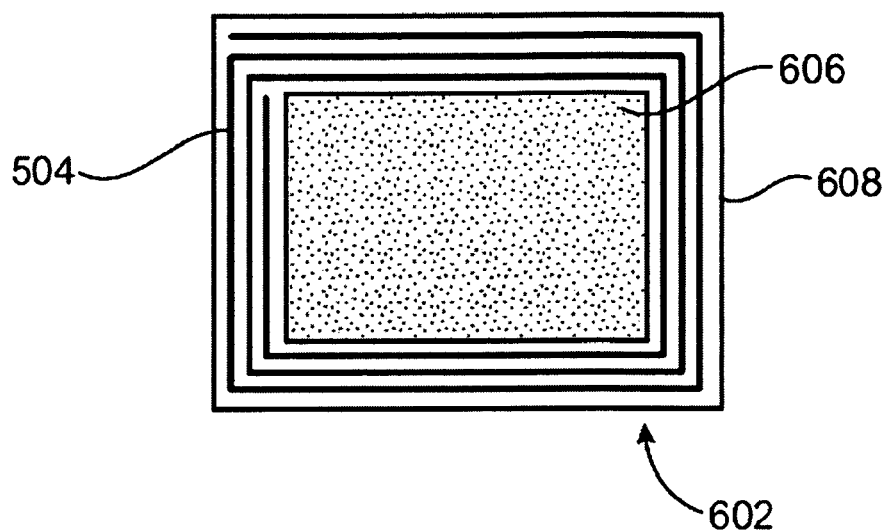
FIGS. 8A to 8B show a first RFID module and a second RFID module, according to one embodiment.
Figure 8B:
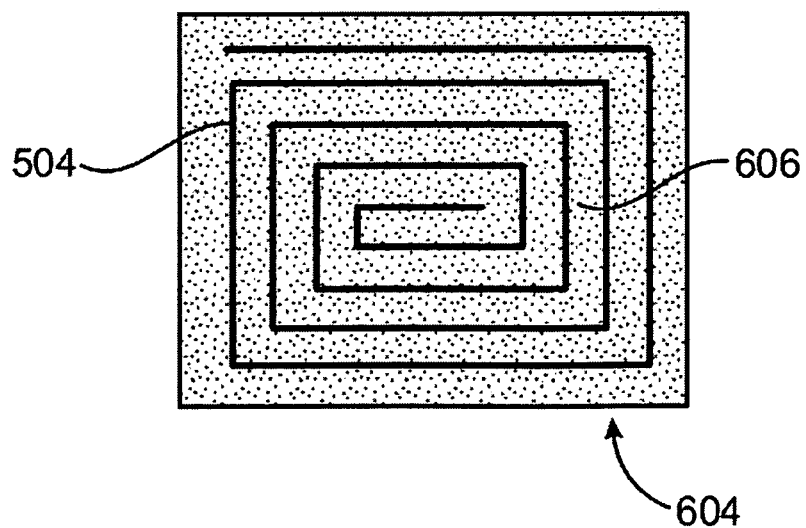

FIGS. 8A and 8B show a first RFID module 602 and a second RFID module 604, according to one embodiment. The first RFID module 602 is configured in association with a small chip 606 (integrated circuit or flexible electrode). The small chip 606 is, for example, between 10 micrometers and 10 millimeters on a side, such as 100 micrometers to 5 millimeters, e.g. one millimeter on a side, having a cathode on a first side (not shown) and an anode on a second side (not shown). The chip 606 is embedded in a skirt 608 by which conductive transmission is generated by modulating current. An antenna 504 runs along, i.e., is associated with, the perimeter of the chip 606. The antenna 504 includes, for example, a multi-turn/multi-layer antenna that acts as the antenna for an RFID link. In one embodiment, the antenna is relatively small. In various embodiments, an insulating layer (not shown) is introduces over the antenna 504 to extend range. For example, the insulting layer includes several hundred microns of plastic over the antenna 504. In this manner, the pharmaceutical RFID unit 602 is compact, and therefore easily ingestible/implantable while still operable in an acceptable communication range. In various other embodiments, the antenna 504 matches a refractive index of the body. In this manner, the RFID antenna facilitates interbody, intrabody, and extrabody communications.

The second RFID module 604 is configured in association with a small chip 606 having a cathode layer (not shown) on top of the chip 606. The layer of metal is patterned with the antenna 504, e.g., densely patterned with the antenna 504 having a multi-turned, spiral-patterned design. The metal layer has slits cut therein, such as single spiral slit cut. When the cathode material is deposited, the antenna 504 serves as a conductor which provides the substrate for attaching the cathode and also the current collector for extracting electrical energy from it. In this manner, the antenna 504 becomes shorted when wet, thus permitting the RFID module to function in a dry environment (manufacturing, pharmacy, etc.) but not in liquid environment, e.g., inside the body. This promotes privacy by disabling RFID communications with the lifecycle pharma informatics system while it is in the body.

In various embodiments, the antenna 504 is configured according to any pattern and/or location respective to the lifecycle pharma informatics system. Patterns include, for example, spirals, squiggles, curves, multi-turned, straight, curved, single layer, multi-layer, and other designs and combinations of designs.

Figure 9:
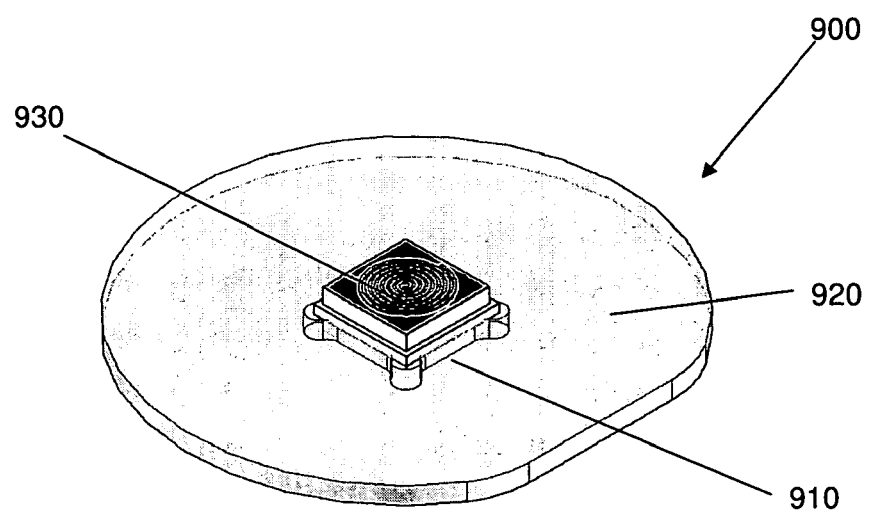
FIG. 9 shows an ingestible event marker identifier that includes a conductive communication module and an RFID communication module, according to one embodiment.

FIG. 9 shows an ingestible event marker identifier that includes an RFID communication module, according to an embodiment. In FIG. 9, IEM identifier 900 includes integrated circuit component 910 and skirt 920. Integrated circuit component 910 includes both a conductive communication module and an RFID communication module. Identifier 910 also includes RFID antenna 930.

IEM identifiers that include both conductive communication modules and non-conductive communication modules, such as RFID communications modules, find use in a variety of different applications which may span the product lifetime of an ingestible event marker. Abilities and functionalities provided by such identifiers include, but are not limited to: reading of IEM identifier information and storing pedigree information at of one or more of the IEM manufacturing stage, supply chain stage, pharmacy management stage, and patient use stage. Complete pedigrees for a given IEM, from manufacture to use and/or disposal may readily be obtained. Audit capability may be provided at every point in the supply chain. Automated sorting gates and cryptographic signatures may be employed to verify product authenticity, as desired.

Figure 10:
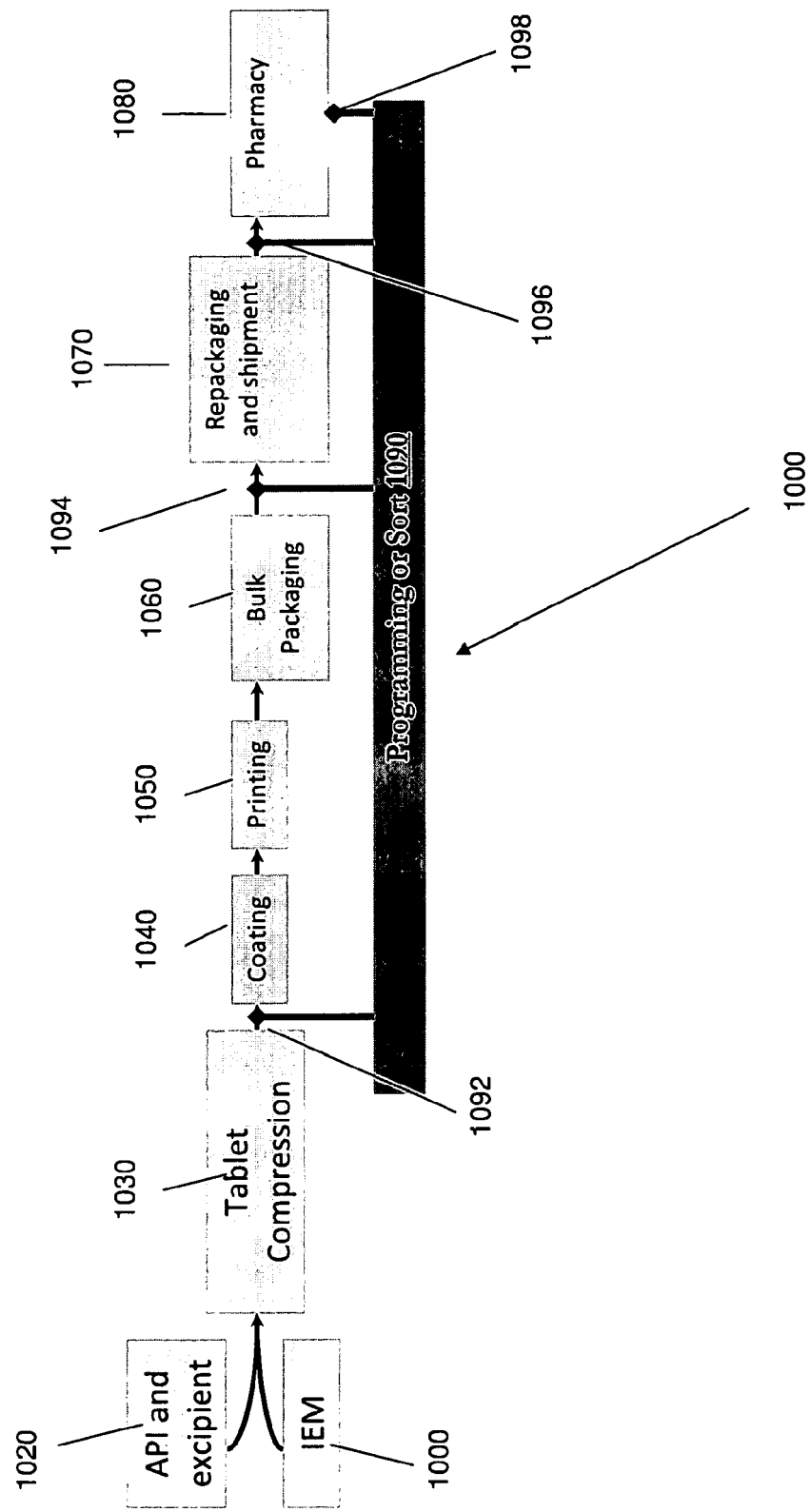
FIG. 10 provides a flow diagram of an IEM product lifetime, according to one embodiment.

IEM devices including both conductive communication and non-conductive communication modules may be fabricated using any convenient manufacturing protocol. In some instances, the manufacturing protocol that is employed is a high-throughput manufacturing protocol. Such high-throughput manufacturing protocols include, but are not limited to, those described in U.S. Provisional Application Ser. No. 61/142,849, the disclosure of which is herein incorporated by reference. One high-throughput manufacturing protocol in which the IEM includes an identifier having both conductive and RFID communication modules and a tablet physiologically acceptable carrier that includes an active pharmaceutical agent is schematically illustrated in FIG. 10. The process 1000 illustrated in FIG. 10 begins with an IEM identifier 1010 that includes and conductive and RFID communication module (such as the identifier illustrated in FIG. 9) being combined with an active pharmaceutical agent (API) and a physiologically acceptable vehicle 1020 into a tablet IEM at stage 1030. Following tablet compression, the resultant tablet may be coated at stage 1040 and any printing or labeling applied at stage 1050 to product the final IEM. Next, the IEM is sent to bulk packaging stage 1060, where the resultant bulk package of IEMs is shipped at stage 1070 to pharmacy 1080 for ultimate sale to a customer. Box 1090 illustrates examples of points in the process where the RFID communication module may be employed to transmit information to the IEM and or receive information from the IEM. For example, programming information may be transmitted to the IEM via the RFID communication module at any of points 1092, 1094, 1096 and 1098. Alternatively and/or in addition to transmitting programming information to the IEM via the RFID communication module at any of points 1092, 1094, 1096 and 1098, identifying information may be retrieved from the IEM at any of these points, e.g., to facilitate packaging, sorting, handling, etc.

Figure 11:
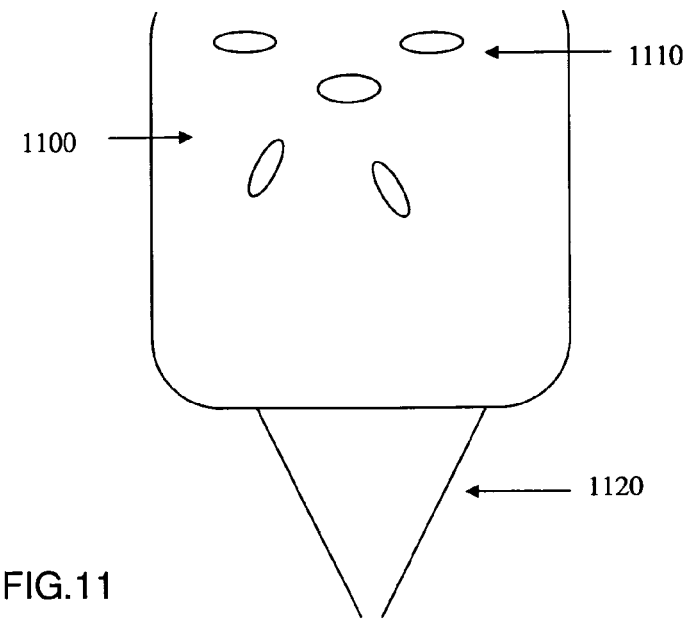
FIG. 11 shows a dispenser that may be used in a manufacturing system, according to one embodiment.
Figure 11:
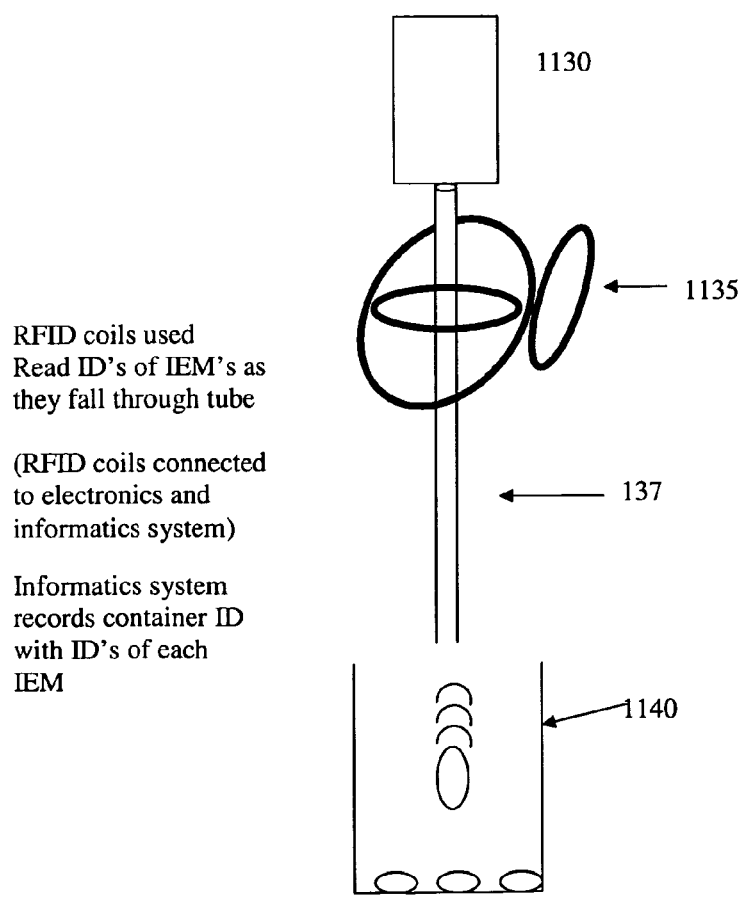

FIG. 11 provides a view of a sorter device that includes an RFID receiver/transmitter, where the sorter device may be used in a manufacturing, and supply chain and/or pharmacy system (for example at any of points 1092, 1094, 1096 and 1098. In FIG. 11, hopper 1100 includes a larger number of IEMs 1110, where the IEMs include both conductive and RFID communication modules, such as the IEM shown in FIG. 9. Funnel 1120 dispenses IEMs into dispenser counter 1130. Dispenser counter 1130 includes 1, 2 or 3 coils 1135 for RFID communication (where three are shown in the figure). Dispenser counter includes tube 1137 which ensures dispensing of a single IEM at a time into container 1140. Container 1140 is filled with identified and sorted IEMs.

Figure 12:
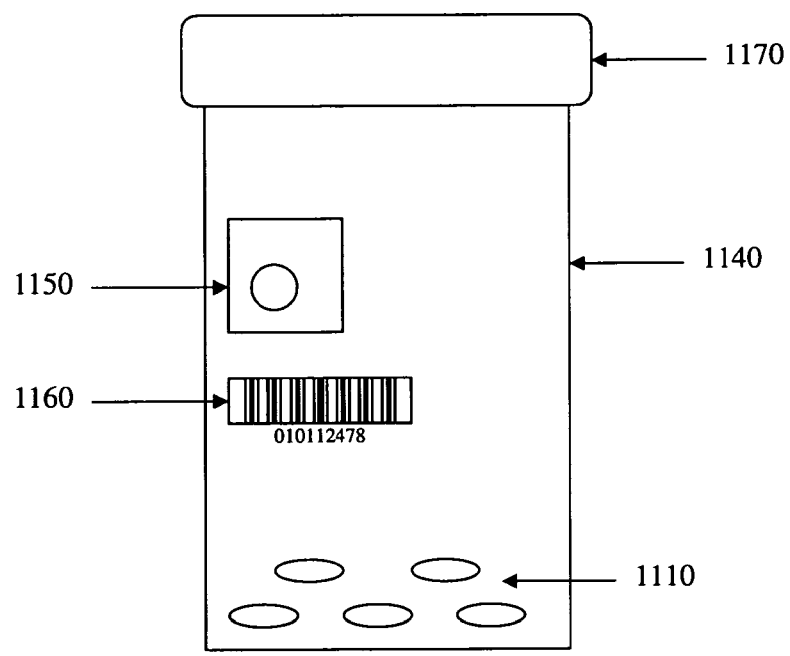
FIG. 12 shows a container that may be produced using the manufacturing system of FIG. 11, according to one embodiment.

An example of an embodiment of container 1140 is shown in FIG. 12. Container 1140 of FIG. 12 includes multiple IEMs 1110 that have been identified by system 1100. Container also includes an RFID tag, 1150 and a bar code 1160. Also shown is cap 1170. The system 1100 and container 1140 may be employed with an informatics system to readily know the exact contents of the container, including the pedigree information for each IEM present in the container.

Figure 13:
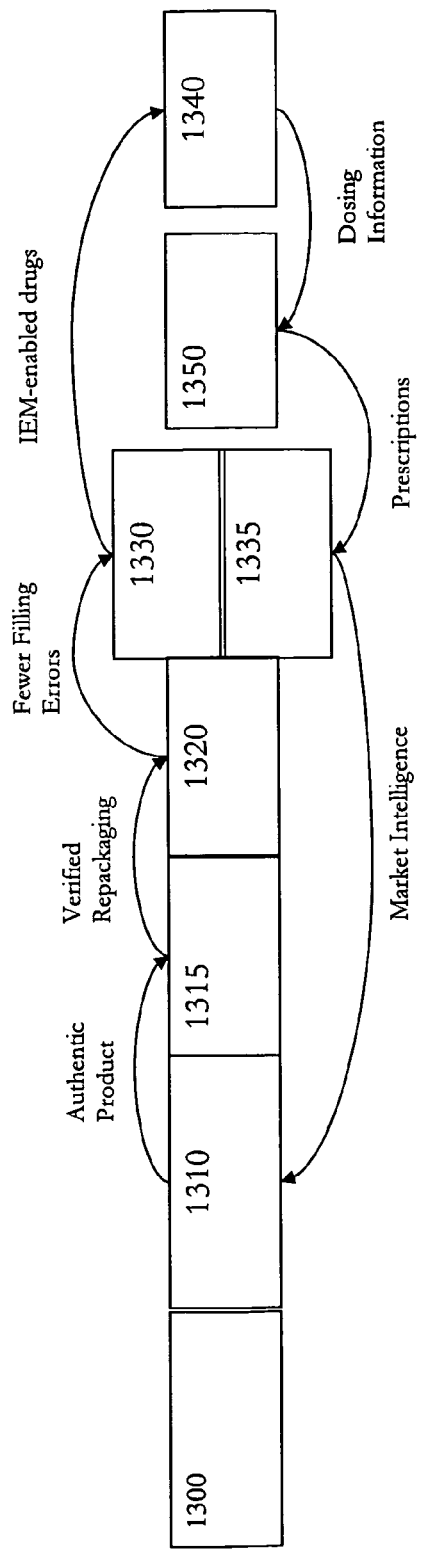
FIG. 13 provides a flow diagram of an IEM product lifetime an illustrates the types of information that may be obtained, according to one embodiment.

FIG. 13 provides a flow diagram of an IEM product lifetime and provides examples of the types of information that be generated by IEM devices that include both conductive and non-conductive communication modules. In FIG. 13, raw materials from raw material suppliers 1300 are sent to manufactures 1310 for manufacture of IEMs. Distributor 1315 and 1320 transfer IEMs from the manufacture to a pharmacy, such as a hospital pharmacy 1330 or retail pharmacy 1335, and ultimately to a patient 1340. Non-conductively communication information may be employed prior to patient ingestion to, among other activities, provide for product authentication the manufacturer 1310 and the first distributor 1315, provide for verified product repackaging between the first distributor 1315 and the second distributor 1320, accurately implement prescription filling at pharmacy 1330 or 1335 with fewer filling errors. Conductively obtained information can be employed to obtain dosing information from the patient 1340 which is employed by health care practitioners 1350 as well as pharmacies (to manage prescriptions) and manufacturers 1310 (for market intelligence, such as sales projections, etc.). Uses of conductively obtained IEM information are further described in PCT Published Application Publication Nos. WO 2006/116718; WO 2008/008281; WO 2008/095183 and WO 2008/063626; the disclosures of which are herein incorporated by reference.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Certain ranges have been presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A device, comprising:
an ingestible component comprising a first communication module, wherein the first communication module is a conductive communication module configured to modulate a first signal, wherein the first signal is a conductive signal communicated through an electrically conductive medium; and
at least a portion of a second communication module configured to modulate a second signal.

2. The device of claim 1, wherein the second communication module is a non-conductive communication module.

3. The device of claim 1, wherein the ingestible component comprises a partial power source comprising a pair of electrodes fabricated from dissimilar materials.

4. The device of claim 1, comprising a second power source electrically coupled to the second communication module.

5. The device of claim 1, wherein the ingestible component comprises the second communication module.

6. The device of claim 1, wherein at least a portion of the second communication module is configured to be separable from the ingestible component in a manner that does not compromise the function of the conductive communication module.

7. The device of claim 1, wherein the ingestible component comprises an active pharmaceutical agent.

8. The device of claim 1, wherein the ingestible component comprises a physiologically acceptable vehicle.

9. A system comprising:
an ingestible component comprising a first communication module, wherein the first communication module is a conductive communication module configured to modulate a first signal, wherein the first signal is a conductive signal communicated through an electrically conductive medium;
at least a portion of a second communication module configured to modulate a second signal; and
a receiver, wherein the receiver, the first communication module, and the second communication module are configured to transmit information between the receiver and at least one of the first or second communication module.

10. The system of claim 9, wherein the receiver comprises a radio-frequency reader.

11. The system of claim 9, wherein the receiver is configured transmit information to the second communication module.

12. The system of claim 9, wherein the receiver is configured to be removably attached to a living being.

13. The system of claim 9, wherein the receiver is an implantable receiver.

14. The system of claim 9, wherein the receiver is configured as an electrical stimulation device.

15. The system of claim 9, wherein the second communication module is a non-conductive communication module.

16. A device, comprising:
an ingestible component comprising a conductive communication module configured to modulate a conductive signal through an electrically conductive medium; and
at least a portion of another module configured to absorb a second signal.

17. The device of claim 16, wherein the other communication module is a non-conductive communication module.

18. The device of claim 16, wherein the ingestible component comprises a partial power source comprising a pair of electrodes fabricated from dissimilar materials.

19. The device of claim 16, comprising a second power source electrically coupled to the second communication module.

20. The device of claim 16, wherein the ingestible component comprises the other communication module.

21. The device of claim 16, wherein at least a portion of the other communication module is configured to be separable from the ingestible component in a manner that does not compromise the function of the conductive communication module.

22. The device of claim 16, wherein the ingestible component comprises an active pharmaceutical agent.

23. The device of claim 16, wherein the ingestible component comprises a physiologically acceptable vehicle.

24. A system comprising:
an ingestible component comprising a conductive communication module configured to modulate a conductive signal through an electrically conductive medium;
at least a portion of another communication module configured to absorb a signal; and
a receiver configured to communicate information between at least one of the conductive communication or the other communication module.

25. The system of claim 24, wherein the receiver comprises a radio-frequency reader.

26. The system of claim 24, wherein the receiver is configured transmit information to the other communication module.

27. The system of claim 24, wherein the receiver is configured to be removably attached to a living being.

28. The system of claim 24, wherein the receiver is an implantable receiver.

29. The system of claim 24, wherein the receiver is configured as an electrical stimulation device.

30. The system of claim 24, wherein the other communication module is a non-conductive communication module.

* * * * *